(12) United States Patent
Ogawa

(10) Patent No.: US 12,007,420 B2
(45) Date of Patent: Jun. 11, 2024

(54) POTENTIAL MEASUREMENT DEVICE

(71) Applicant: SONY SEMICONDUCTOR SOLUTIONS CORPORATION, Kanagawa (JP)

(72) Inventor: Koji Ogawa, Kanagawa (JP)

(73) Assignee: SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 259 days.

(21) Appl. No.: 17/435,315

(22) PCT Filed: Feb. 28, 2020

(86) PCT No.: PCT/JP2020/008226
§ 371 (c)(1),
(2) Date: Aug. 31, 2021

(87) PCT Pub. No.: WO2020/189222
PCT Pub. Date: Sep. 24, 2020

(65) Prior Publication Data
US 2022/0137106 A1 May 5, 2022

(30) Foreign Application Priority Data
Mar. 19, 2019 (JP) .............................. JP2019-051653

(51) Int. Cl.
*G01R 19/257* (2006.01)
*G01R 19/25* (2006.01)
(Continued)

(52) U.S. Cl.
CPC ....... *G01R 19/257* (2013.01); *G01R 19/2509* (2013.01); *H03F 1/26* (2013.01);
(Continued)

(58) Field of Classification Search
CPC .... G01R 19/00; G01R 19/25; G01R 19/2506; G01R 19/2509; G01R 19/257;
(Continued)

(56) References Cited

U.S. PATENT DOCUMENTS 6,462,528 B1 10/2002 Markozen
2011/0193809 A1 8/2011 Walley et al.
(Continued)

FOREIGN PATENT DOCUMENTS

CA 2939287 A1 10/2015
CN 1335511 A 2/2002
(Continued)

OTHER PUBLICATIONS

International Search Report and Written Opinion of PCT Application No. PCT/JP2020/008226, dated Jun. 9, 2020, 12 pages of ISRWO.
(Continued)

*Primary Examiner* — Hoai-An D. Nguyen
(74) *Attorney, Agent, or Firm* — CHIP LAW GROUP

(57) ABSTRACT

Provided is a potential measurement device including: a first substrate having read electrodes arranged in a two-dimensional array; and a second substrate on which the first substrate is stacked, in which each of the read electrodes includes at least one or more AD conversion circuits each having independent correspondence to the read electrode, and at least a part of the AD conversion circuits is arranged in a two-dimensional array on the second substrate.

11 Claims, 16 Drawing Sheets

(51) Int. Cl.
  *H03F 1/26* (2006.01)
  *C12M 1/34* (2006.01)
  *G01N 27/30* (2006.01)
(52) U.S. Cl.
  CPC ......... *C12M 1/3407* (2013.01); *G01N 27/301* (2013.01); *H03F 2200/21* (2013.01); *H03F 2200/504* (2013.01)
(58) Field of Classification Search
  CPC ........ G01N 27/00; G01N 27/26; G01N 27/28; G01N 27/30; G01N 27/301; H03F 1/00; H03F 1/26; H03F 3/00; H03F 3/45; H03F 3/45071; H03F 3/45475; H03F 2200/00; H03F 2200/21; H03F 2200/261; H03F 2200/504; H03M 1/00; H03M 1/06; H03M 1/0602; H03M 1/0604; H03M 1/0607; H03M 1/121205; H03M 1/123; H03M 1/50; H03M 1/56; C12M 41/00; C12M 41/46; C12M 1/00; C12M 1/34; C12M 1/3407
  See application file for complete search history.

(56) References Cited

U.S. PATENT DOCUMENTS

| | | |
|---|---|---|
| 2014/0061488 A1 | 3/2014 | Sato et al. |
| 2014/0175592 A1 | 6/2014 | Iwabuchi et al. |
| 2015/0138153 A1 | 5/2015 | Walley et al. |
| 2015/0270580 A1* | 9/2015 | Habuta .................. H01G 11/56 427/553 |
| 2015/0275287 A1 | 10/2015 | Tian |
| 2016/0013763 A1 | 1/2016 | Tomimatsu et al. |
| 2017/0061187 A1* | 3/2017 | Wen .................... G06V 40/1306 |
| 2019/0158032 A1 | 5/2019 | Takano et al. |

FOREIGN PATENT DOCUMENTS

| | | |
|---|---|---|
| CN | 1838423 A | 9/2006 |
| CN | 103654807 A | 3/2014 |
| CN | 106029897 A | 10/2016 |
| EP | 1158302 A2 | 11/2001 |
| EP | 2720453 A2 | 4/2014 |
| JP | 59-126306 A | 7/1984 |
| JP | 09-246880 A | 9/1997 |
| JP | 2002-31617 A | 1/2002 |
| JP | 2002-055144 A | 2/2002 |
| JP | 2014-049983 A | 3/2014 |
| JP | 2014-195112 A | 10/2014 |
| JP | 2016-019235 A | 2/2016 |
| JP | 2016-171455 A | 9/2016 |
| JP | 2017-507653 A | 3/2017 |
| KR | 10-2006-0096924 A | 9/2006 |
| TW | 201101476 A | 1/2011 |
| WO | 2006/129762 A1 | 12/2006 |
| WO | 2015/148127 A1 | 10/2015 |
| WO | 2016/152267 A1 | 9/2016 |
| WO | WO-2019058815 A1 * | 3/2019 ........... G01N 27/414 |

OTHER PUBLICATIONS

Obien, et al., "Revealing neuronal function through microelectrode array recordings", Frontiers in Neuroscience, vol. 8, Jan. 6, 2015, 30 pages.

Park, et al., "A High-Density CMOS Multi-Modality Joint Sensor/Stimulator Array with 1024 Pixels for Holistic Real-Time Cellular Characterization", Symposium on VLSI Circuits Digest of Technical Papers, 2016, 02 pages.

* cited by examiner

FIG.2
WITH VARIATION IN OFFSET
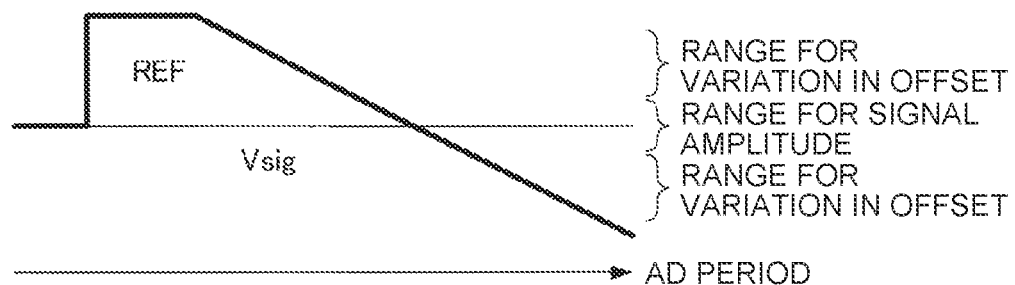
WITH VARIATION IN OFFSET
(i)
→ IMPROVEMENT IN SAMPLING RATE
(ii)
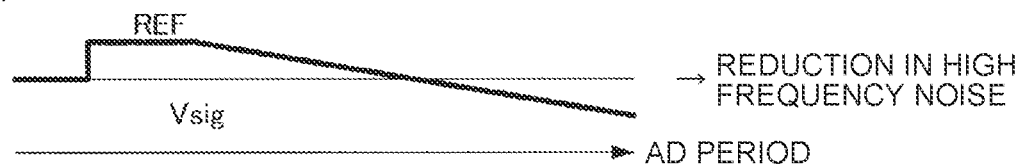
→ REDUCTION IN HIGH FREQUENCY NOISE

POTENTIAL MEASUREMENT DEVICE

CROSS REFERENCE TO RELATED APPLICATIONS

This application is a U.S. National Phase of International Patent Application No. PCT/JP2020/008226 filed on Feb. 28, 2020, which claims priority benefit of Japanese Patent Application No. JP 2019-051653 filed in the Japan Patent Office on Mar. 19, 2019. Each of the above-referenced applications is hereby incorporated herein by reference in its entirety.

FIELD

The present disclosure relates to a potential measurement device.

BACKGROUND

There is a device that arranges microelectrodes in an array and measures the potential of a solution on the microelectrodes. Among such devices, there is a device in which a microelectrode is filled with a culture solution, a biological cell is placed, and an action potential generated by the biological cell is measured (refer to Patent Literature 1, for example). In recent years in particular, there is a noteworthy device having an electrode, an amplifier, an AD converter, and the like, integrated into one chip using a complementary MOS (CMOS) integrated circuit technology so as to simultaneously measure the potentials at multiple points (refer to Non Patent Literature 1, for example).

In consideration of the acquisition of action potential waveforms of nerve cells, low-noise measurement of several μV class is supposedly required while achieving a sampling rate of about 10 kHz or more. Furthermore, in order to achieve detailed and wide-ranging acquisition of signal propagation in a nerve cell network, it is necessary to densely spread the electrodes with an electrode size of approximately 10 μm square to achieve high resolution. Noise reduction, high sampling rate, and high resolution are in trade-off, and various proposals have been made in a circuit architecture to overcome the trade-off (refer to Non Patent Literature 1, for example).

As one of promising techniques for achieving low noise and high resolution, a configuration has been proposed in which while a differential amplifier circuit is provided for each of electrodes, an amplifier circuit region (reference circuit region) on one side constituting the differential amplifier circuit is separated from another amplifier circuit region (read circuit region) from which a signal received by the electrode is read (refer to Non Patent Literature 2, for example).

CITATION LIST

Patent Literature

Patent Literature 1: JP 2002-31617 A

Non Patent Literature

Non Patent Literature 1: M. Obien, et al., "Revealing neuronal function through microelectrode array recordings", Frontiers in Neuro ScienceVol. 8 (2015) Article 423

Non Patent Literature 2: J. Park, et al., "A High-Density CMOS Multi-Modality JointSensor/Stimulator Array with 1024 Pixels for Holistic Real-Time Cellular Characterization", Symposium on VLSI Circuits Digest of Technical Papers (2016)

SUMMARY

Technical Problem

Unfortunately, however, these methods have a configuration in which the read circuit/reference circuit, the load PMOS, the current source NMOS, and the A/D conversion circuit of the amplifier circuit are physically separated from each other, making it difficult to prevent individual node wiring lines of the amplifier circuit from being long-distance wiring along with acquisition of high resolution. The long-distance wiring lines leads to deterioration in noise due to an increase in wiring resistance and deterioration in a sampling rate due to an increase in wiring capacitance. In addition, a difference in the wiring length of the amplifier circuit for each of cells would lead to variation in offset. An increase in the AD period due to the variation in offset would also cause deterioration of the sampling rate.

Therefore, the present disclosure proposes a novel and improved potential measurement device capable of achieving further facilitated data processing and higher analysis accuracy while suppressing deteriorations in noise and the sampling rate, and the variation in offset.

Solution to Problem

According to the present disclosure, a potential measurement device is provided that includes: a first substrate having read electrodes arranged in a two-dimensional array; and a second substrate on which the first substrate is stacked, wherein each of the read electrodes includes at least one or more AD conversion circuits each having independent correspondence to the read electrode, and at least a part of the AD conversion circuits is arranged in a two-dimensional array on the second substrate.

BRIEF DESCRIPTION OF DRAWINGS

FIG. 2 is a diagram illustrating an example of comparing an AD conversion time between a case with a variation in offset and a case with no variation in offset.

DESCRIPTION OF EMBODIMENTS

Preferred embodiments of the present disclosure will be described in detail hereinbelow with reference to the accompanying drawings. Note that redundant descriptions will be omitted from the present specification and the drawings by assigning the same reference signs to components having substantially the same functional configuration.

Note that the description will be provided in the following order.
1. Embodiments of present disclosure
1.1. Background
1.2. Configuration examples and operation examples
2. Summary

1. Embodiments of Present Disclosure

[1.1. Background]
Before describing embodiments of the present disclosure in detail, the background of how the present disclosers have conceived the embodiments of the present disclosure will be described.

As described above, there is a noteworthy device in recent years in which an electrode, an amplifier, an AD converter, and the like are integrated into one chip using CMOS integrated circuit technology, and potentials are simultaneously measured at multiple points. Noise reduction, high sampling rate, and high resolution are in trade-off, and there have been various proposals related to a circuit architecture in order to overcome the trade-off.

Figure 1:
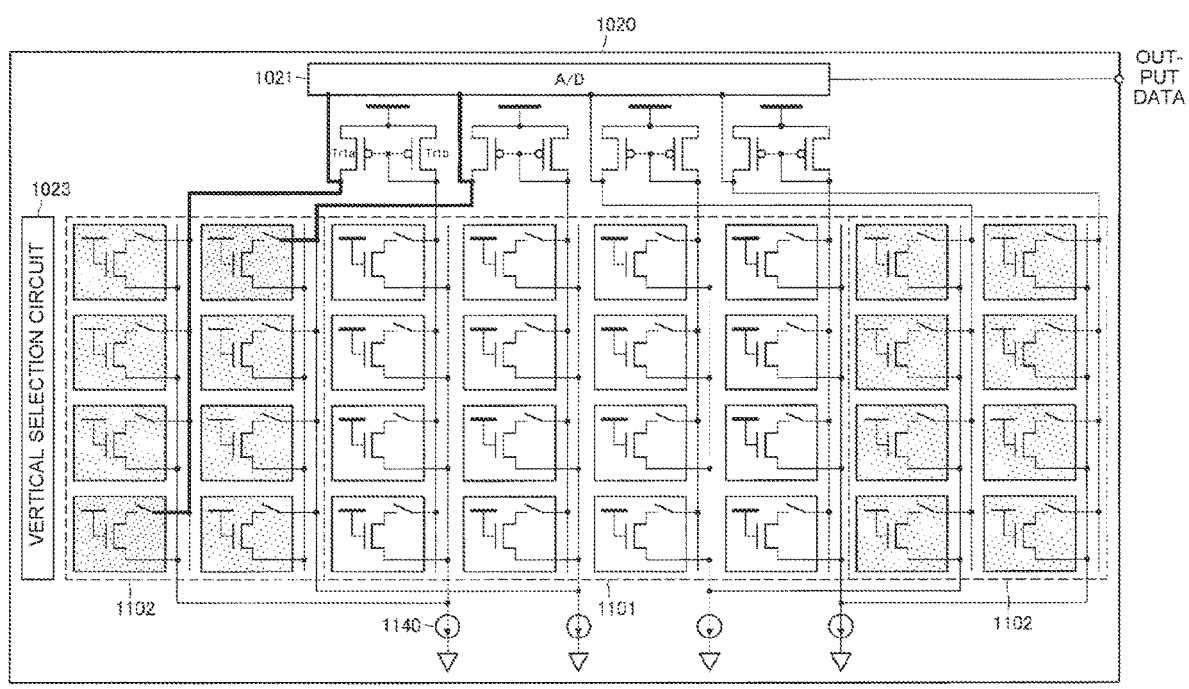
FIG. 1 is a diagram illustrating a circuit configuration example of an existing potential measurement device.

FIG. 1 is a diagram illustrating a circuit configuration example of an existing potential measurement device. A potential measurement device 1020 illustrated in FIG. 1 is a device capable of simultaneously detecting potentials at multiple points, and has a configuration in which a read circuit region and a reference circuit region are separated from each other. The potential measurement device 1020 illustrated in FIG. 1 includes: an A/D conversion circuit 1021; a vertical selection circuit 1023; and a semiconductor device including a read cell region 1101 and a reference cell region 1102. FIG. 1 also illustrates MOSFETs Tr$1a$ and Tr$1b$ constituting a current mirror, and a current source 1140.

The A/D conversion circuit 1021 is a circuit that converts analog data measured by the semiconductor device into digital data. The vertical selection circuit 1023 is a circuit that outputs a signal for selecting a read cell or a reference cell used for measuring the potential to the semiconductor device.

In the potential measurement device having such a configuration, input referred noise can be reduced by obtaining a certain degree of amplification gain in the first stage differential amplifier circuit. However, when a certain degree of amplification gain is obtained in the first stage differential amplifier circuit, the output resistance would be higher than that in a case where the source follower circuit is used as the first stage amplifier. Furthermore, in order to achieve high resolution while maintaining a high sampling rate, it is necessary to increase the number of parallel configurations in the AD conversion circuit, and it is necessary to connect the output of the differential amplifier circuit, which has a high output resistance, to the AD conversion circuit arranged outside the electrode array by long-distance wiring (that is, high parasitic capacitance).

In this manner, the configuration that separates the read circuit region and the reference circuit region from each other would result in a long distance between the output of the differential amplifier circuit in the reference circuit region and the AD conversion circuit. This would deteriorate the settling time of the output of the differential amplifier circuit, making the configuration incompatible with the improvement of the sampling rate.

Moreover, in a case where increasing the number of parallel configurations of the AD conversion circuit causes mismatching between the width of the electrode array and the width of the region of the AD conversion circuit, the variation in the wiring length becomes large between the electrodes, leading to variation in offset of the differential amplifier output caused by the wiring resistance. Here, assuming a single-slope AD converter which is configurable with a small area, an increase in variation in offset of the differential amplifier output is directly linked with an increase in AD conversion time.

FIG. 2 is a diagram illustrating an example of comparing an AD conversion time between a case with a variation in offset and a case with no variation in offset. This is because the AD conversion method illustrated in FIG. 2 is a method of implementing AD conversion by comparing, by the single-slope AD converter, a reference signal that changes with time with an input analog signal (differential amplifier output), and thus needs to secure a range for the variation in offset in addition to the range for signal amplitude. As illustrated in FIG. 2, an increase in the AD conversion time means a decrease in the sampling rate. In addition, when there is no variation in offset, the high frequency noise can be reduced by increasing the AD conversion time. However, when there is variation in offset, it is necessary to further increase the AD conversion time in order to reduce the high frequency noise.

In view of the above points, the present disclosers have conducted intensive studies on an architecture of a potential measurement device for overcoming the trade-off between noise reduction, high sampling rate, and high resolution. As a result, the present disclosers have devised an architecture of a potential measurement device capable of suppressing deterioration in noise and the sampling rate, and variation in offset, as described below.

[1.2. Configuration Examples and Operation Examples]

Next, a configuration example of the potential measurement device according to the embodiment of the present disclosure will be described. The potential measurement device according to the embodiment of the present disclosure has a structure including: a substrate (first substrate) on which an electrode array is arranged; and a second substrate on which an AD conversion circuit array is arranged and which is stacked with respect to the first substrate. The potential measurement device according to the embodiment of the present disclosure is characterized by arranging the area for an AD conversion circuit to be positioned immediately below an electrode. With such a configuration, the potential measurement device according to the embodiment of the present disclosure can minimize the wiring length from the output of the amplifier circuit to the AD conversion circuit, and can substantially equalize the length of each of wiring lines. Accordingly, the potential measurement device according to the embodiment of the present disclosure can improve the sampling rate by reducing the wiring capacitance, and can also improve the sampling rate by reducing the variation in offset of the amplifier output, which can be achieved by substantially equalizing the wiring length that has been different for each of cells.

Figure 3:
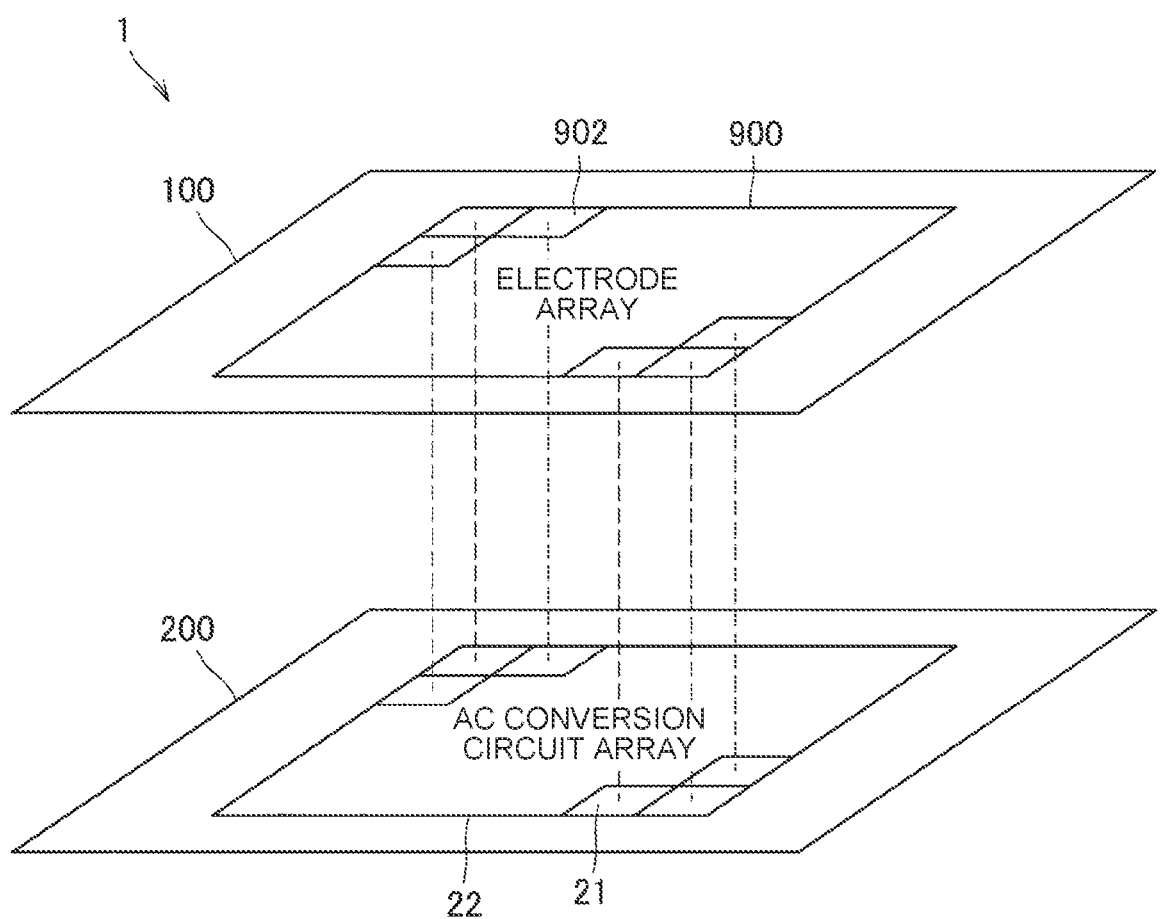
FIG. 3 is a diagram illustrating a schematic configuration of a potential measurement device according to an embodiment of the present disclosure.

FIG. 3 is a diagram illustrating a schematic configuration of the potential measurement device according to the embodiment of the present disclosure. As described above, a potential measurement device 1 illustrated in FIG. 3 has a structure in which a first substrate 100 and a second substrate 200 are stacked. The first substrate 100 includes a read electrode array 900 in which electrodes 902 are arranged in an array. The second substrate 200 includes an AD conversion circuit array 22 corresponding to the read electrode array 900 of the first substrate 100. The AD conversion circuit array 22 has an array of AD conversion circuits 21 corresponding to the respective electrodes of the first substrate 100. The read electrode array 900 and the AD conversion circuit array 22 are connected to each other with electrical conduction. This connection with electrical conduction is achieved by a wafer level Cu—Cu bonding technique, for example. With a structure in which the first substrate 100 and the second substrate 200 are stacked, the wiring length between the electrode 902 and the AD conversion circuit corresponding to the electrode can be made substantially equal in all the cells.

Figure 4:
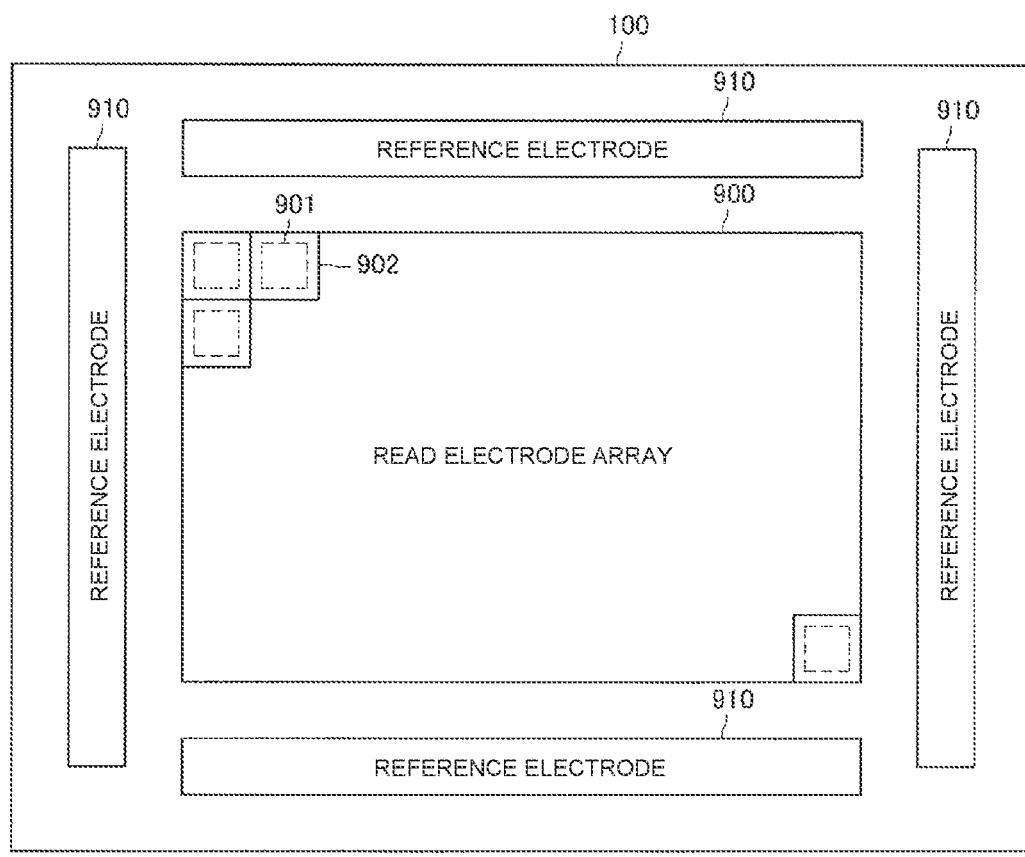
FIG. 4 is a diagram illustrating a schematic configuration of a first substrate 100 of a potential measurement device 1 according to the embodiment of the present disclosure.

FIG. 4 is a diagram illustrating a schematic configuration of the first substrate 100 of the potential measurement device 1 according to the embodiment of the present disclosure. The read electrode array 900 provided on the first substrate 100 includes, as components, the electrodes 902 and the amplifier circuits 901 arranged as many as the electrodes 902 at the same pitch as the electrodes 902. In addition, a reference electrode 910 is arranged outside the read electrode array 900. The reference electrode 910 is an electrode provided to give a reference potential to a culture solution (culture medium) of a measurement target cell in which the read electrode array 900 is immersed. The potential measurement device 1 according to the embodiment of the present disclosure measures a displacement from a reference potential supplied by the reference electrode 910 as an action potential of the measurement target cell.

Figure 5:
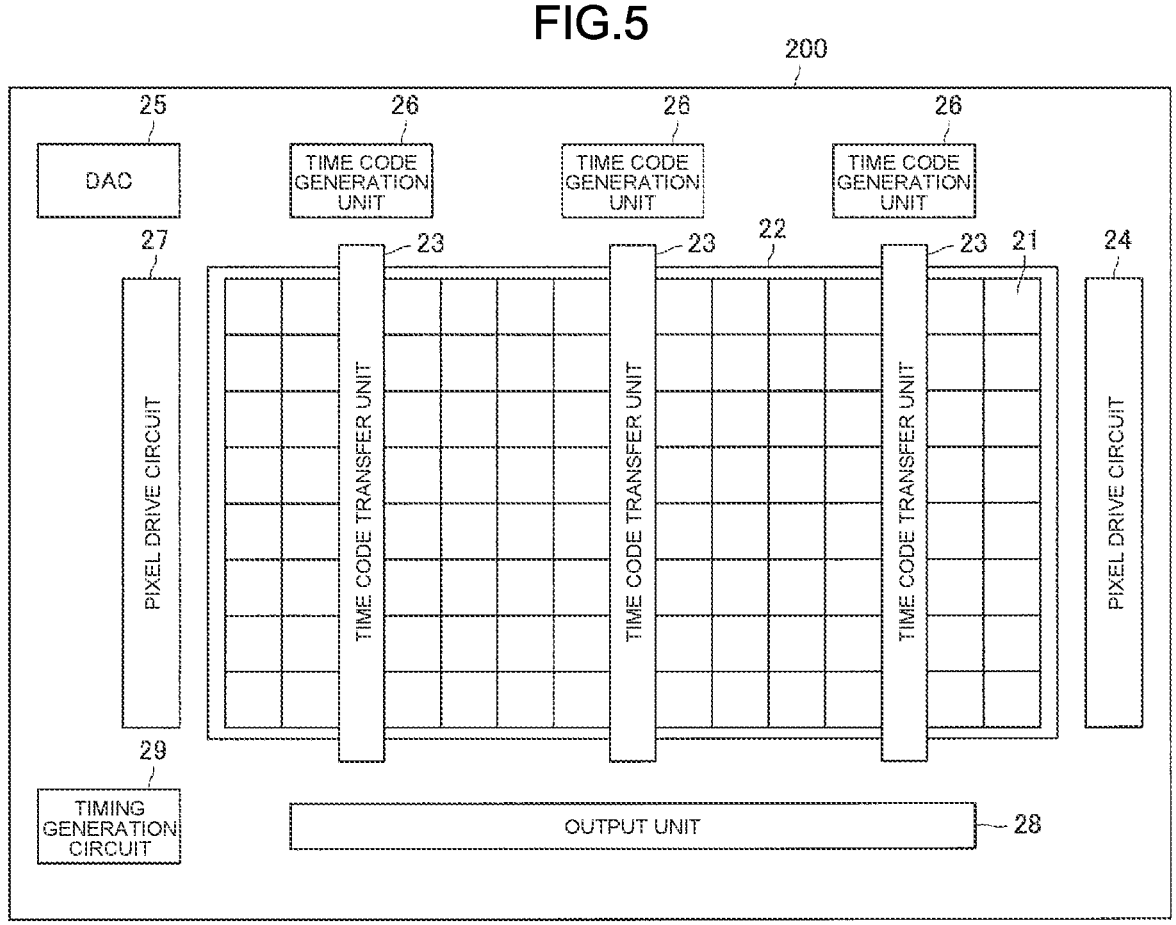
FIG. 5 is a diagram illustrating a schematic configuration of a second substrate 200 of the potential measurement device 1 according to the embodiment of the present disclosure.

FIG. 5 is a diagram illustrating a schematic configuration of the second substrate 200 of the potential measurement device 1 according to the embodiment of the present disclosure. As described above, the first substrate 100 is stacked on the second substrate 200. The second substrate 200 includes the AD conversion circuit array 22 corresponding to the read electrode array 900 of the first substrate 100. Various circuits necessary for operating the AD conversion circuits 21 are arranged outside the AD conversion circuit array 22.

The AD conversion circuit array 22 also includes time code transfer units 23 that transfer time codes generated by time code generation units 26 to each of the AD conversion circuits 21. In addition, a pixel drive circuit 24, a D/A converter (DAC) 25, the time code generation units 26, a vertical drive circuit 27, an output unit 28, and a timing generation circuit 29 are formed around the AD conversion circuit array 22 on the second substrate 200.

The AD conversion circuits 21 arranged in a two-dimensional array convert an analog signal from the electrode 902 into a digital signal SIG and output the digital signal SIG.

The pixel drive circuit 24 drives the AD conversion circuit 21. The DAC 25 generates a reference signal (reference voltage signal) REF, which is a slope signal whose level (voltage) monotonously decreases with the lapse of time, and supplies the reference signal REF to each of the AD conversion circuits 21. The time code generation unit 26 generates a time code to be used when each of the AD conversion circuits 21 converts an analog signal into a digital signal (AD conversion), and supplies the generated time code to the corresponding time code transfer unit 23. A plurality of time code generation units 26 is provided with respect to the AD conversion circuit array 22, and within the AD conversion circuit array 22, as many the time code transfer units 23 as the number corresponding to the time code generation units 26 are provided. That is, the time code generation units 26 and the time code transfer units 23 that transfer the time codes generated by the time code generation units 26 have one-to-one correspondence.

The vertical drive circuit 27 controls the output unit 28 to output the digital signal SIG generated in the AD conversion circuit 21 in a predetermined order based on the timing signal supplied from the timing generation circuit 29. The digital signal SIG output from the AD conversion circuit 21 is then output from the output unit 28 to the outside of the potential measurement device 1. The output unit 28 performs predetermined digital signal processing such as a black level correction process of correcting a black level and a correlated double sampling (CDS) process as necessary, and then outputs the processed signal to the outside.

The timing generation circuit 29 includes a timing generator that generates various timing signals or the like, and supplies the generated various timing signals to the pixel drive circuit 24, the DAC 25, the vertical drive circuit 27, and the like.

Figure 6:
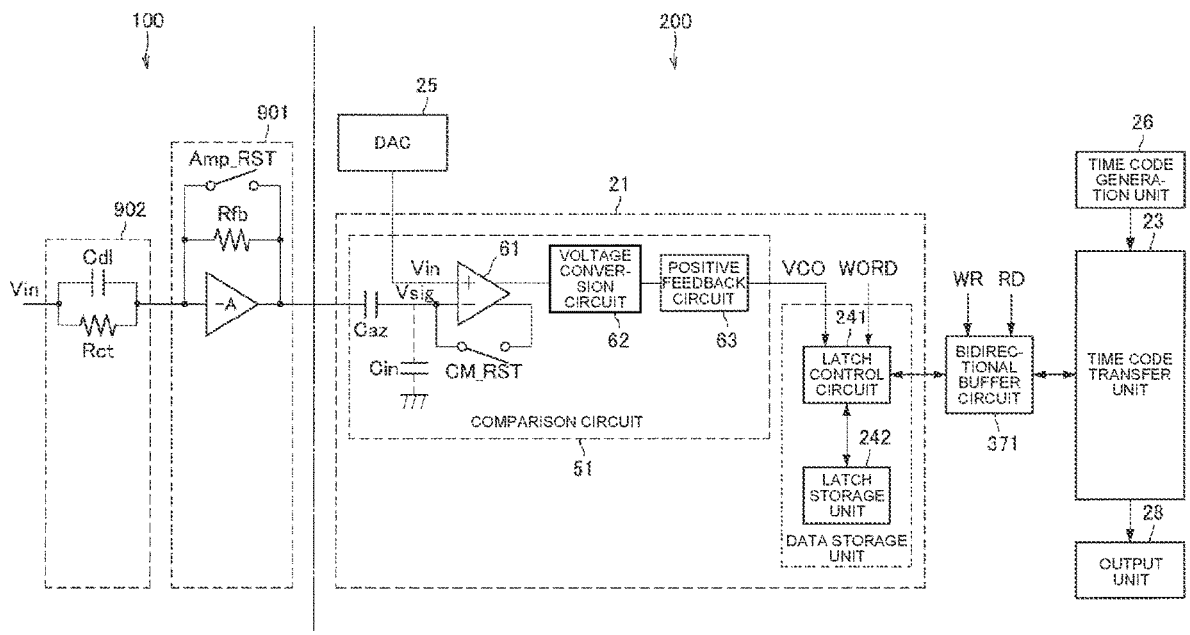
FIG. 6 is a diagram illustrating a circuit block diagram for portions from an electrode 902 to an AD conversion circuit 21.
Figure 7:
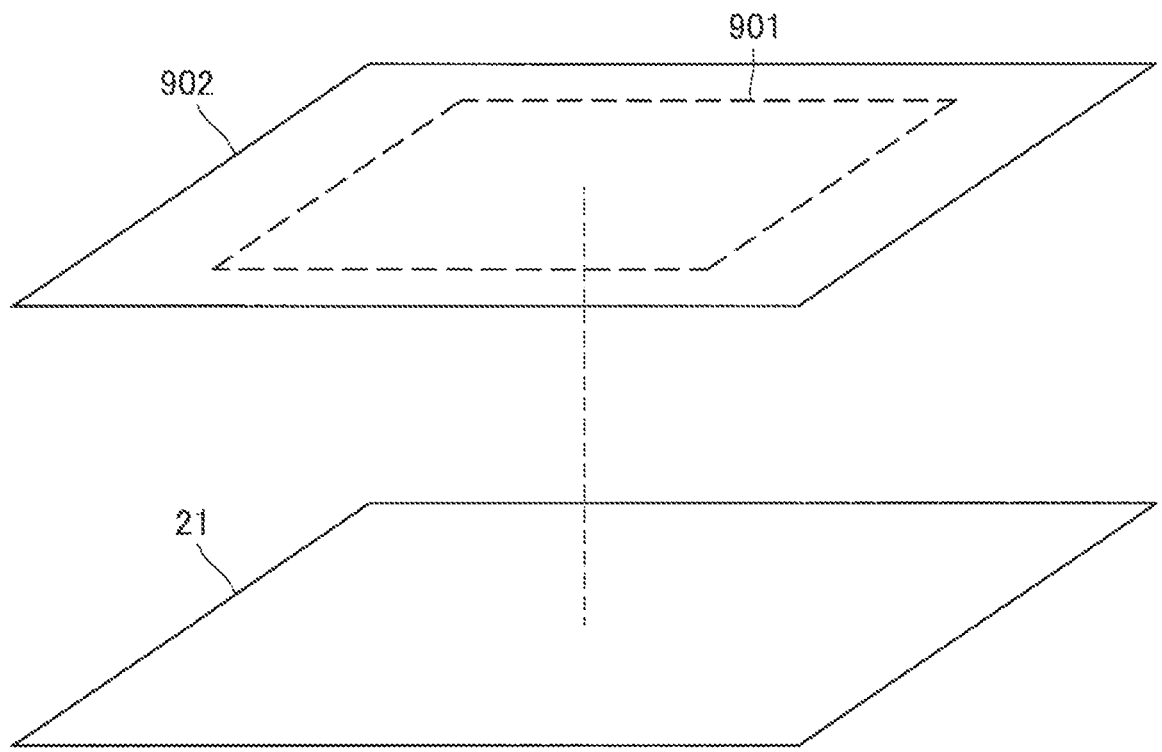
FIG. 7 is a diagram illustrating an outline of a stacked structure of the electrode 902 and an amplifier circuit 901, and the AD conversion circuit 21.

FIG. 6 is a diagram illustrating a circuit block diagram for portions from the electrode 902 to the AD conversion circuit 21, which is formed across the first substrate 100 and the second substrate 200. FIG. 7 is a diagram illustrating an outline of a stacked structure of the electrode 902 and the amplifier circuit 901, and the AD conversion circuit 21. The electrode 902 adopts, as a circuit model, a simplest model in which capacitance Cd1 mainly representing the effect of the electric double layer capacitance and resistance Rct mainly representing the effect of the charge transfer resistance are connected in parallel.

The amplifier circuit 901 having an open-loop gain of −A times is connected to a subsequent stage of the electrode 902. The input/output connection of the amplifier circuit 901 is made via a feedback resistor Rfb. The feedback resistor Rfb is formed by using a non-doped polysilicon resistor, for example. More desirably, the feedback resistor Rfb can be configured as a variable resistor. In addition, a reset switch transistor is connected to the input/output of the amplifier circuit 901 so that the input/output of the amplifier circuit 901 can be short-circuited at the time of reset. The on/off control of this reset transistor is made by a signal Amp_RST.

The output wiring of the amplifier circuit 901 is passed to the second substrate 200. An analog signal from the amplifier circuit 901 is first sent to a comparison circuit 51 of the AD conversion circuit 21. The comparison circuit 51 compares a reference signal REF supplied from the DAC 25 with the analog signal sent from the amplifier circuit 901 of the first substrate 100, and then outputs an output signal VCO as a comparison result signal indicating a comparison result. When the reference signal REF and the analog signal have a same level (same voltage), the comparison circuit 51 inverts the output signal VCO.

The comparison circuit 51 includes a differential input circuit 61, a voltage conversion circuit 62, and a positive feedback (PFB) circuit 63.

A data storage unit 52 receives an input of the output signal VCO from the comparison circuit 51, and further receives a supply of a WORD signal that controls the read timing of the AD conversion circuit 21 during the signal read operation, from the vertical drive circuit 27. In addition, the time code generated by the time code generation unit 26 is also supplied to the data storage unit 52 via the time code transfer unit 23.

The data storage unit 52 includes a latch control circuit 241 that controls the write operation and the read operation of the time code based on the WORD signal, and a latch storage unit 242 that stores the time code.

In the time code write operation, the latch control circuit 241 stores, in the latch storage unit 242, the time code which is supplied from the time code transfer unit 23 and updated every unit time, during the time of inputting a Hi (indicating High) output signal VCO from the comparison circuit 51. When the reference signal REF and the signal SIG have a same level (same voltage) and the output signal VCO supplied from the comparison circuit 51 is inverted to Lo (indicating Low), the latch control circuit 241 stops writing (updating) of the supplied time code, and controls to allow the time code last stored in the latch storage unit 242 to be held in the latch storage unit 242. The time code stored in the latch storage unit 242 represents a time when the analog signal and the reference signal REF become equal, and represents data indicating that the analog signal is the reference voltage at that time, that is, a digitized light quantity value.

After the sweep of the reference signal REF is completed and the time codes have been stored in the latch storage units 242 of all the AD conversion circuits 21 in the AD conversion circuit array 22, the operation of the AD conversion circuit 21 is changed from the write operation to the read operation.

In the time code read operation, when the AD conversion circuit 21 reaches its own read timing, the latch control circuit 241 outputs the time code (digital signal SIG) stored in the latch storage unit 242 to the time code transfer unit 23 based on the WORD signal that controls the read timing. The time code transfer unit 23 sequentially transfers the supplied time code in the column direction (vertical direction) so as to be supplied to the output unit 28.

Hereinafter, in order to distinguish from the time code to be written in the latch storage unit 242 in the time code write operation, digitized data indicating that the analog signal is the reference voltage at that time, which is an inverting time code when the output signal VCO read from the latch storage unit 242 is inverted in the time code read operation, will be also referred to as AD conversion data.

A bidirectional buffer circuit 37 is provided corresponding to a shift register included in the time code transfer unit 23. The bidirectional buffer circuit 371 is connected to one D flip-flop in the corresponding shift register.

The bidirectional buffer circuit 371 is supplied with a write control signal WR that becomes Hi in the time code write operation and is supplied with a read control signal RD that becomes Hi in the time code read operation. The bidirectional buffer circuit 371 switches the write operation and the read operation of the time code based on the write control signal WR and the read control signal RD.

The analog signal from the amplifier circuit 901 is connected to an inverting input terminal of the differential input circuit 61 of the comparison circuit 51 at the first stage of the AD conversion circuit 21 via a DC cut capacitance Caz. The DC cut capacitance Caz is provided in a case where a reset operation (also referred to as auto zero AZ) of the comparison circuit 51 is performed. By performing this reset operation, the input offset caused by the manufacturing variation of the comparison circuit 51 can be canceled.

Although the above has described an example in which one amplifier circuit 901 and one AD conversion circuit 21 correspond to one electrode 902, the present disclosure is not limited to such an example. The potential measurement device 1 may have a configuration in which one amplifier circuit 901 and one AD conversion circuit 21 correspond to a plurality of electrodes 902.

Figure 8:
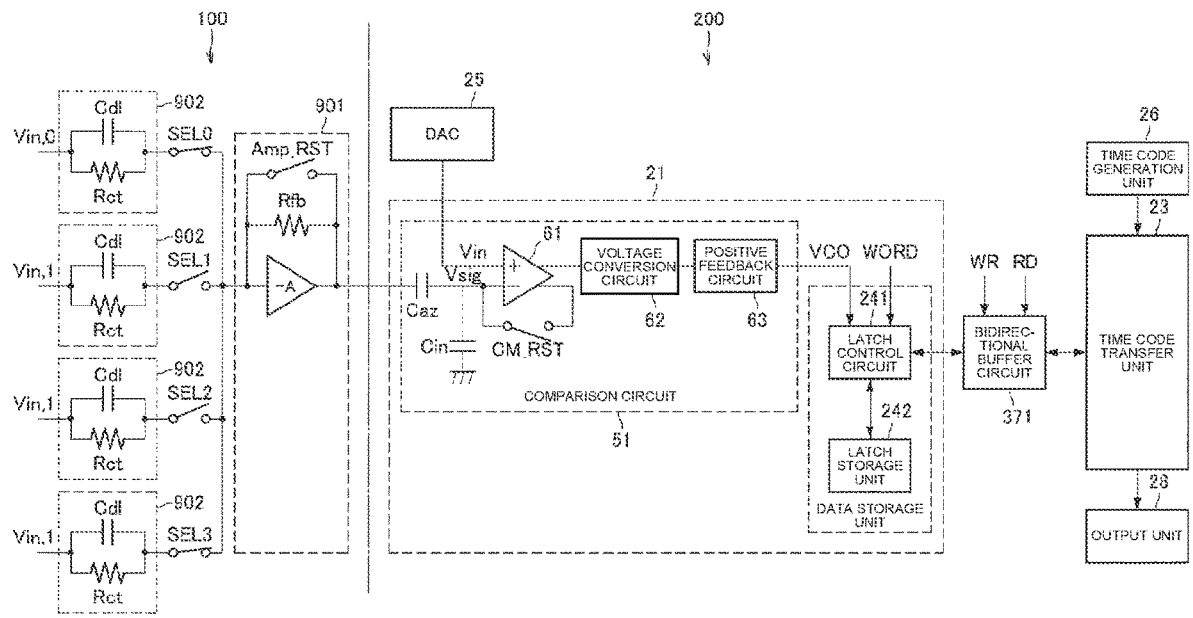
FIG. 8 is a diagram illustrating a circuit block diagram for portions from the electrode 902 to the AD conversion circuit 21.
Figure 9:
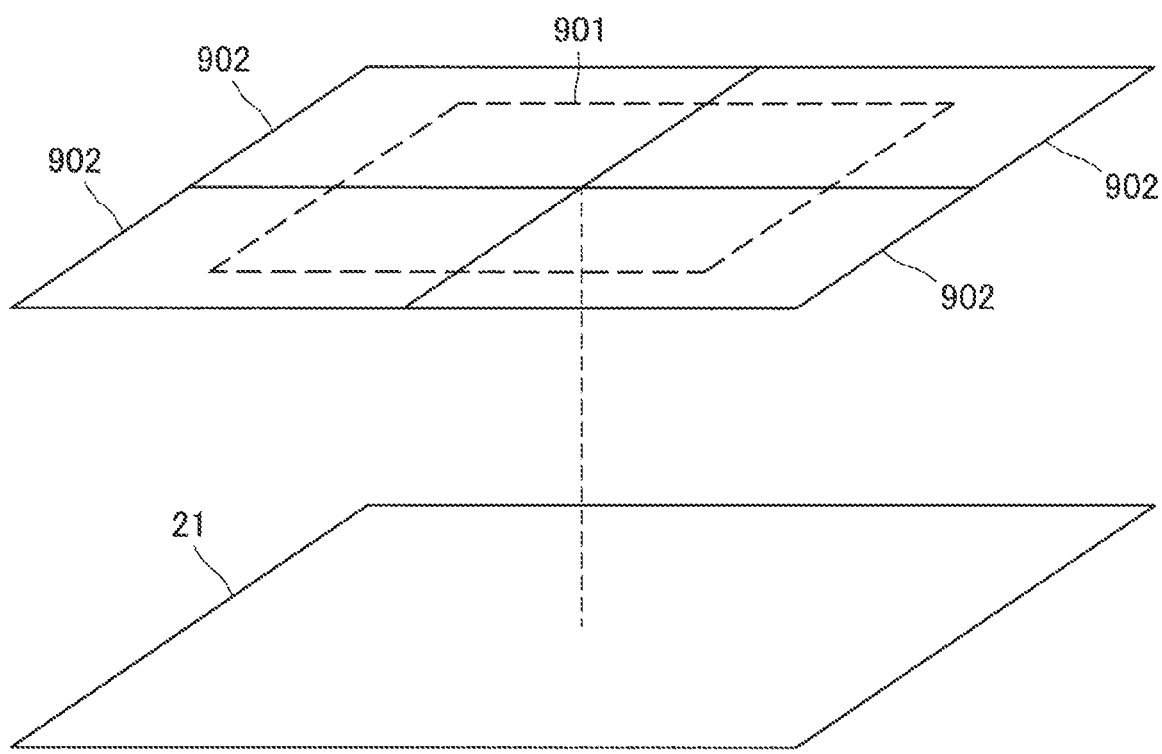
FIG. 9 is a diagram illustrating an outline of a stacked structure of four electrodes 902 and one amplifier circuit 901, and one AD conversion circuit 21.

FIG. 8 is a diagram illustrating a circuit block diagram for portions from the electrode 902 to the AD conversion circuit 21, which is formed across the first substrate 100 and the second substrate 200. FIG. 8 illustrates an example in which one amplifier circuit 901 and one AD conversion circuit 21 correspond to four electrodes 902. FIG. 9 is a diagram illustrating an outline of a stacked structure of four electrodes 902 and one amplifier circuit 901, and one AD conversion circuit 21.

Figure 10:
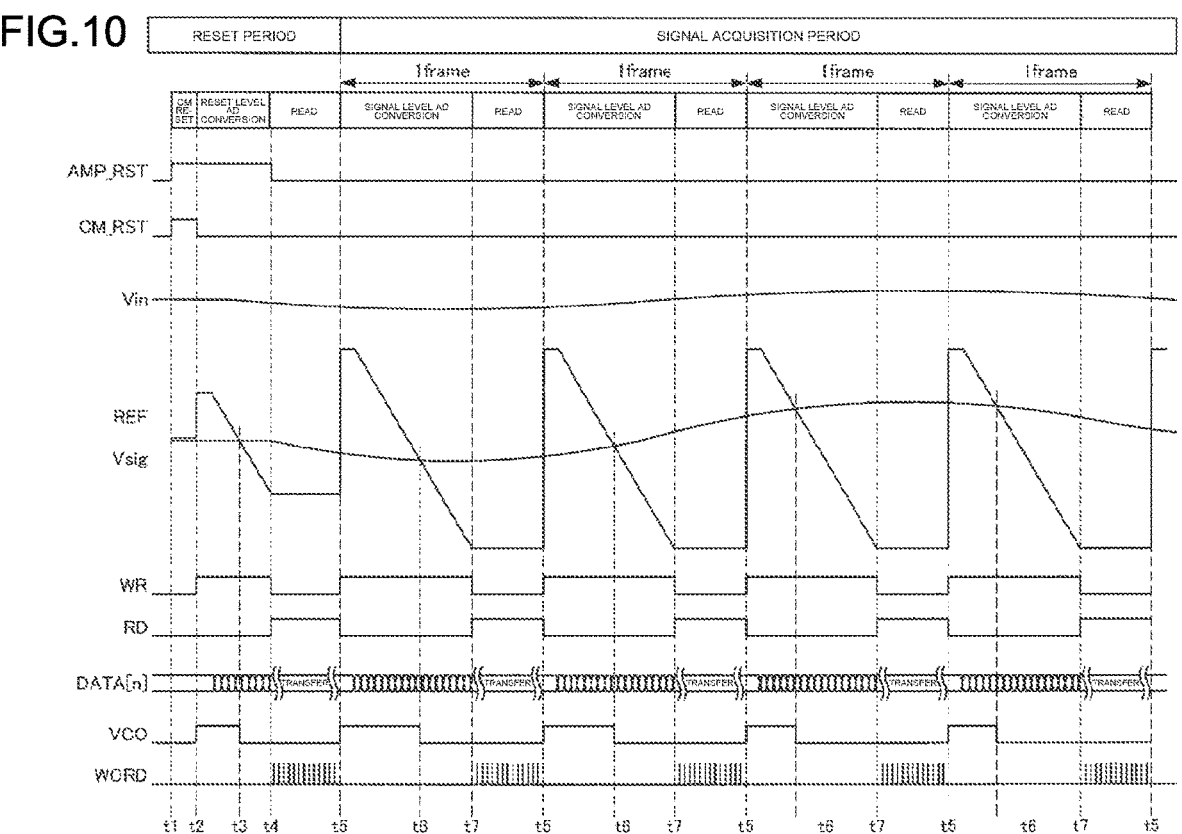
FIG. 10 is a diagram in a timing chart illustrating operation of the potential measurement device 1 according to the embodiment of the present disclosure.

Next, an operation example of the potential measurement device 1 according to the embodiment of the present disclosure will be described. FIG. 10 is a diagram in a timing chart illustrating operation of the potential measurement device 1 according to the embodiment of the present disclosure.

The potential measurement device 1 according to the embodiment of the present disclosure requires a reset period prior to a signal acquisition period. The reset period corresponds to times t1 to t5. The signal acquisition period corresponds to time t5 or later.

The potential measurement device 1 according to the embodiment of the present disclosure continuously acquires signals of a plurality of frames (for example, several hundred frames) during the signal acquisition period. Thereafter, the potential measurement device 1 according to the embodiment of the present disclosure inserts the reset period again as a refresh period. Subsequently, the potential measurement device 1 according to the embodiment of the present disclosure drives to start the signal acquisition period again.

In the reset period, the potential measurement device 1 according to the embodiment of the present disclosure starts the reset operation of the amplifier circuit and the comparison circuit at time t1. At the following time t2, the potential measurement device 1 finishes resetting the comparison circuit, and raises a reference signal REF and a write enable signal WR to the latch storage unit of time code DATA [n] in order to start AD conversion of the reset level. At time t3, signals REF and Vsig changing in a slope shape cross each other, and a comparator output VCO is inverted. Together with this, the time code DATA [n] written in the latch storage unit 242 at that point is to be stored in the latch storage unit 242. The stored time code will be a reset level AD conversion result.

At time t4, the AD conversion period of the reset level ends, the reset signals Amp_RST and WR of the amplifier circuit 901 fall, and instead, an enable signal RD for reading the AD conversion result stored in the latch storage unit 242 to the time code transfer unit 23 rises. A period from time t4 to t5 is a period in which the AD conversion result of the reset level is read to the time code transfer unit 23 by the WORD signal and then read to the output unit 28 via the time code transfer unit 23.

At time t5, the reset period ends, and the first frame of the signal acquisition period starts. The signal acquisition period is similar to the reset period except that the reset signal Amp_RST of the amplifier circuit 901 and the reset signal CM_RST of the comparison circuit 51 are not driven and the time for AD conversion is longer (due to a wider signal level range than the reset level).

Times t5, t6, and t7 correspond to times t2, t3, and t4, respectively. The subsequent operations will be the repetition of the operations from time t5 to time t7, and thus the description thereof will be omitted.

Note that the potential measurement device 1 according to the embodiment of the present disclosure can also implement correlated double sampling (CDS) by arranging frame memory in the output unit 28, holding the AD conversion result of the reset level acquired during the reset period, and obtaining a difference from the AD conversion result of the signal level acquired during the signal acquisition period.

FIGS. 11 to 14 are diagrams illustrating a circuit configuration example of the amplifier circuit 901.

Figure 11:
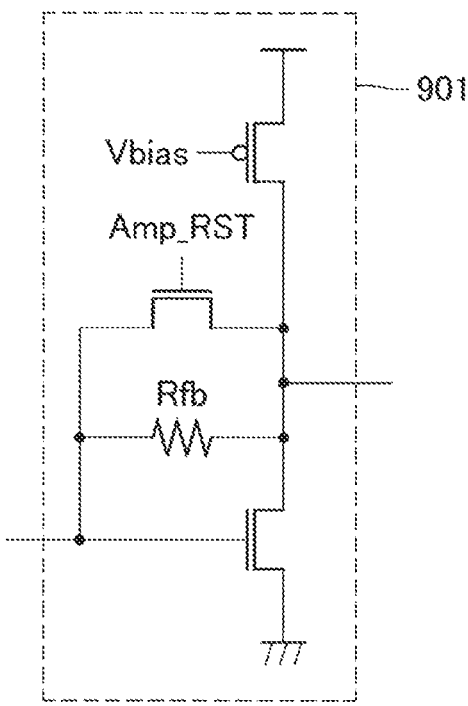
FIG. 11 is a diagram illustrating a circuit configuration example of the amplifier circuit 901.

In the amplifier circuit 901 illustrated in FIG. 11, the feedback resistor Rfb and a reset transistor driven by the Amp_RST signal are connected to a common-source amplifier circuit.

Figure 12:
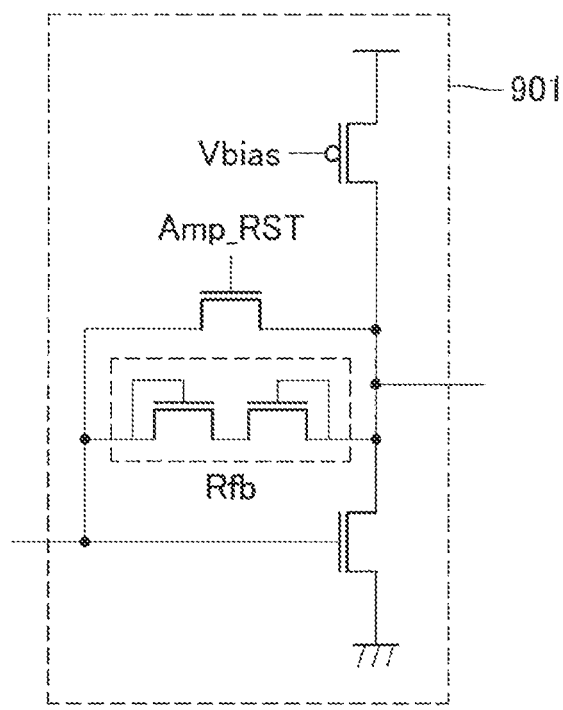
FIG. 12 is a diagram illustrating a circuit configuration example of the amplifier circuit 901.

The amplifier circuit 901 illustrated in FIG. 12 uses a bidirectional normally-off transistor as the feedback resistor Rfb. By using a bidirectional normally-off transistor as the feedback resistor Rfb, the feedback resistor Rfb of the amplifier circuit 901 can obtain a high resistance value with a small area.

Figure 13:
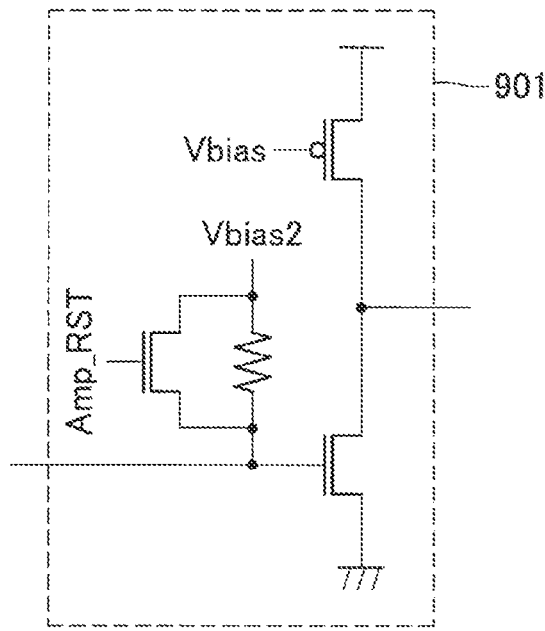
FIG. 13 is a diagram illustrating a circuit configuration example of the amplifier circuit 901.

The amplifier circuit 901 illustrated in FIG. 13 has a configuration similar to the example illustrated in FIG. 11 except for the circuit configuration of the amplifier. In the amplifier circuit 901 illustrated in FIG. 13, an input node of an amplifier is connected to a bias voltage Vbias2 via a resistor, instead of using the feedback resistor Rfb. The bias voltage Vbias2 is a bias voltage that can be arbitrarily set by the user. Therefore, in the amplifier circuit 901 illustrated in FIG. 13, the user can arbitrarily adjust an operating point of the amplifier.

Figure 14:
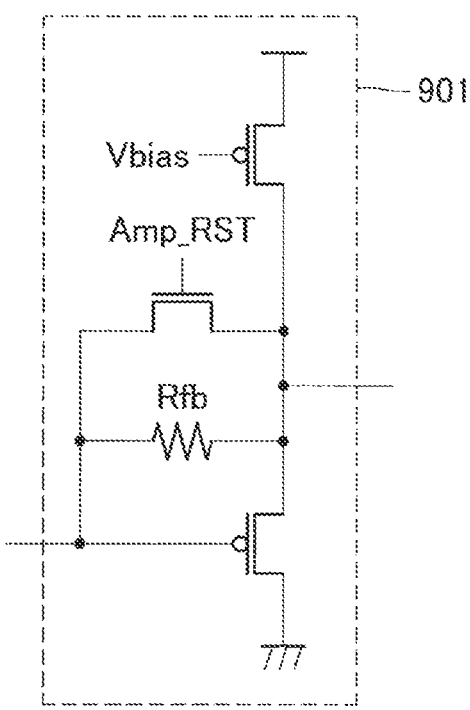
FIG. 14 is a diagram illustrating a circuit configuration example of the amplifier circuit 901.

The amplifier circuit 901 illustrated in FIG. 14 has a configuration similar to the example illustrated in FIG. 11 except for the circuit configuration of the amplifier. The amplifier circuit 901 illustrated in FIG. 14 uses a source follower circuit instead of the common-source amplifier circuit. The amplifier circuit 901 illustrated in FIG. 14 can expand a use range by using a source follower circuit as an amplifier. The expansion of the use range is useful in measuring cells having a larger signal amplitude compared to nerve cells, such as cardiomyocytes.

Figure 15:
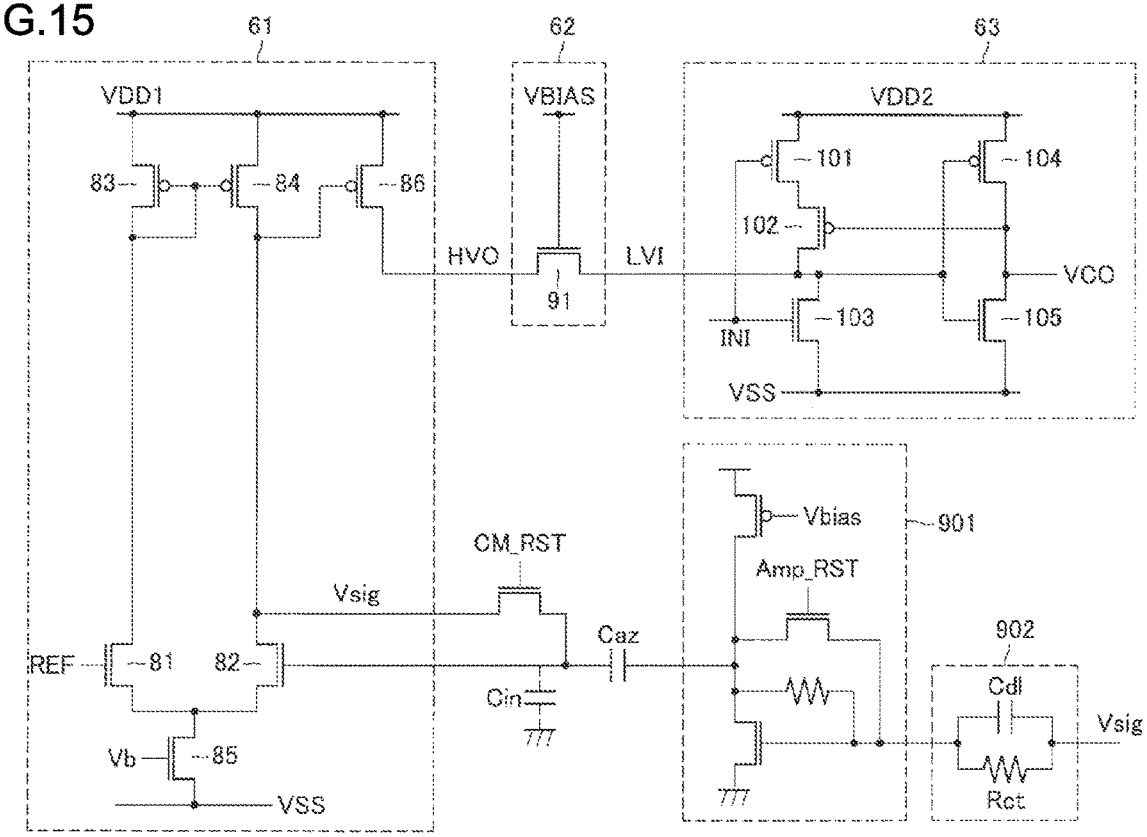
FIG. 15 is a diagram illustrating a circuit configuration for portions from the electrode 902 to a comparison circuit 51.

FIG. 15 is a diagram illustrating a circuit configuration for portions from the electrode 902 to the comparison circuit 51.

FIG. 15 is a circuit diagram in which details of the electrode 902 and one amplifier circuit 901 are added to the comparison circuit 51 illustrated in FIG. 6.

The differential input circuit 61 compares the signal SIG output from the amplifier circuit 901 with the reference signal REF output from the DAC 25, and outputs a predetermined signal (current) when the signal SIG is higher than the reference signal REF.

The differential input circuit 61 includes: transistors 81 and 82 forming a differential pair; transistors 83 and 84 constituting a current mirror; a transistor 85 as a constant current source that supplies a current IB according to an input bias current Vb; and a transistor 86 that outputs an output signal HVO of the differential input circuit 61.

The transistors 81, 82, and 85 are negative channel MOS (NMOS) transistors, and the transistors 83, 84, and 86 are positive channel MOS (PMOS) transistors.

Among the transistors 81 and 82 forming the differential pair, the reference signal REF output from the DAC 25 is input to the gate of the transistor 81, while the signal SIG output from the amplifier circuit 901 is input to the gate of the transistor 82. The sources of the transistor 81 and the transistor 82 are connected to the drain of the transistor 85, while the source of the transistor 85 is connected to a predetermined voltage VSS (VSS<VDD2<VDD1).

The drain of the transistor 81 is connected to the gates of the transistors 83 and 84 and the drain of the transistor 83 constituting the current mirror circuit, while the drain of the transistor 82 is connected to the drain of the transistor 84 and the gate of the transistor 86. The sources of the transistors 83, 84, and 86 are connected to a first power supply voltage VDD1.

The voltage conversion circuit 62 is constituted with an NMOS transistor 91, for example. The drain of the transistor 91 is connected to the drain of the transistor 86 of the differential input circuit 61, the source of the transistor 91 is connected to a predetermined connection point in a positive feedback circuit 63, and the gate of the transistor 86 is connected to a bias voltage VBIAS.

The transistors 81 to 86 constituting the differential input circuit 61 are a circuit that operates at a high voltage up to the first power supply voltage VDD1, and the positive feedback circuit 63 is a circuit that operates at a second power supply voltage VDD2 lower than the first power supply voltage VDD1. The voltage conversion circuit 62 converts the output signal HVO input from the differential input circuit 61 into a low voltage signal (conversion signal) LVI at which the positive feedback circuit 63 can operate, and supplies the converted signal to the positive feedback circuit 63.

The bias voltage VBIAS may be any voltage that allows the voltage to be converted into a voltage that would not destroy individual transistors 101 to 105 of the positive feedback circuit 63 operating at a constant voltage. For example, the bias voltage VBIAS can be set to the same voltage as the second power supply voltage VDD2 of the positive feedback circuit 63 (VBIAS=VDD2).

The positive feedback circuit 63 outputs a comparison result signal that is inverted when the signal SIG is higher than the reference signal REF based on the conversion signal LVI obtained by converting the output signal HVO from the differential input circuit 61 into a signal corresponding to the second power supply voltage VDD2. In addition, the positive feedback circuit 63 increases the transition rate at the inversion of the output signal VCO output as the comparison result signal.

The positive feedback circuit 63 is constituted with the five transistors 101 to 105. Here, the transistors 101, 102, and 104 are PMOS transistors, and the transistors 103 and 105 are NMOS transistors.

The source of the transistor 91, which is an output terminal of the voltage conversion circuit 62, is connected to the drains of the transistors 102 and 103 and the gates of the transistors 104 and 105. The sources of the transistors 101 and 104 are connected to the second power supply voltage VDD2, the drain of the transistor 101 is connected to the source of the transistor 102, and the gate of the transistor 102 is connected to the drains of the transistors 104 and 105 which are also output terminals of the positive feedback circuit 63. The sources of the transistors 103 and 105 are connected to the predetermined voltage VSS. An initialization signal INI is supplied to the gates of the transistors 101 and 103.

The transistors 104 and 105 constitute an inverter circuit, and a connection point between the drains of these is an output terminal at which the comparison circuit 51 outputs the output signal VCO.

Figure 16:
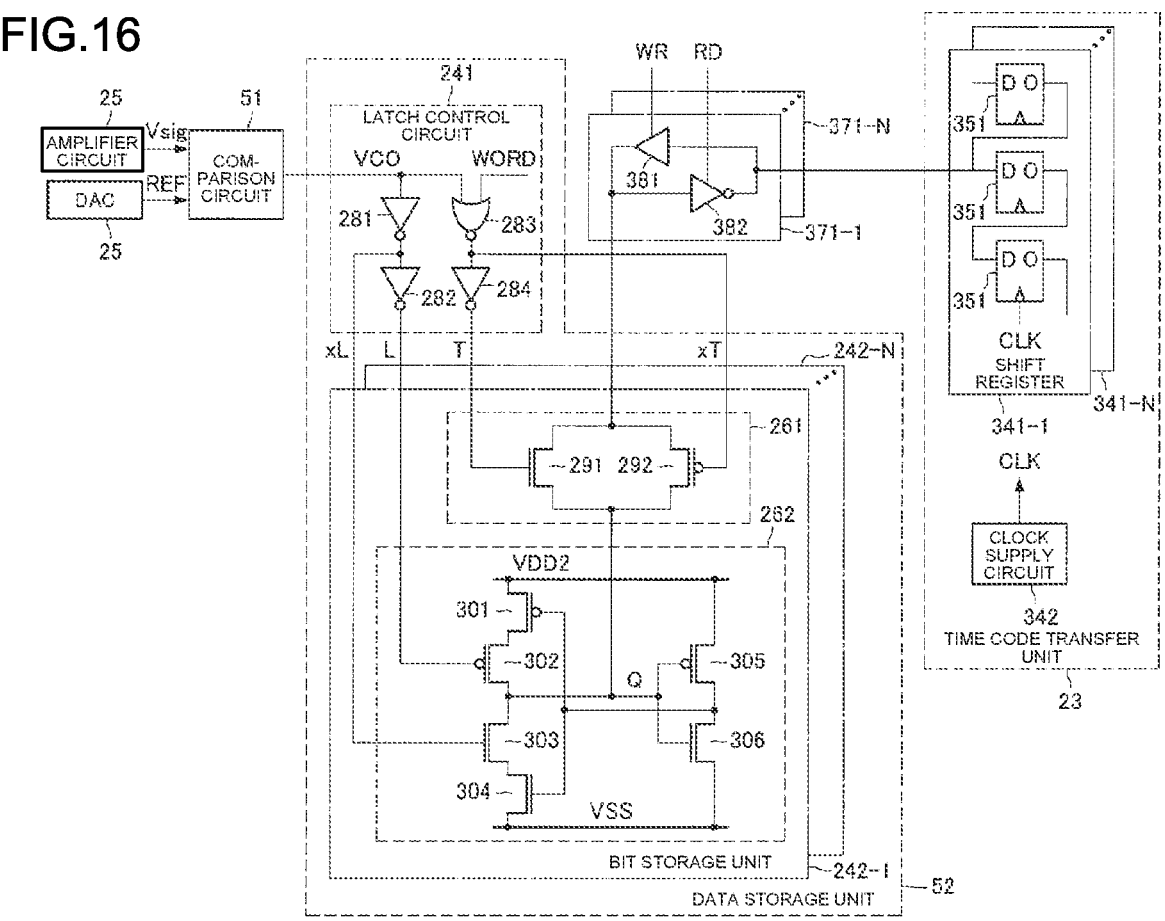
FIG. 16 is a diagram illustrating a circuit configuration for portions from a data storage unit 52 to a time code transfer unit 23.

FIG. 16 is a diagram illustrating a circuit configuration for portions from the data storage unit 52 to the time code transfer unit 23.

The time code transfer unit 23 includes N shift registers 341-1 to 341-N corresponding to N-bit time codes DATA [1] to DATA [N], and a clock supply circuit 342. Each of the N shift registers 341-1 to 341-N includes a plurality of D-flip-flops (D-F/Fs) 351. The clock supply circuit 342 supplies a clock signal CLK to the clock input of each of the D-F/Fs 351 of the shift register 341.

The data storage unit 52 includes the latch control circuit 241 and N bit storage units 242-1 to 242-N. Furthermore, N bidirectional buffer circuits 371-1 to 371-N are provided between the time code transfer unit 23 and the data storage unit 52.

The N bidirectional buffer circuits 371-1 to 371-N are provided in one-to-one correspondence with the N shift registers 341-1 to 341-N of the time code transfer unit 23. The bidirectional buffer circuit 371 is connected to one D-F/F 351 in the corresponding shift register 341.

A buffer circuit 381 in the bidirectional buffer circuit 371-$n$ is supplied with the write control signal WR that becomes Hi in the time code write operation, while an inverter circuit 382 is supplied with the read control signal RD that becomes Hi in the time code read operation. The bidirectional buffer circuit 371-$n$ switches the write operation and the read operation of the time code toward the bit storage unit 242-$n$ based on the write control signal WR and the read control signal RD.

One latch control circuit 241 supplies the output signal VCO and the WORD signal to the N bit storage units 242-1 to 242-N. Each of the bit storage units 242-1 to 242-N includes a transfer gate 261 and a latch storage unit 262.

The latch control circuit 241 includes two inverters 281 and 282 connected in series, and a NOR circuit 283 and an inverter 284 connected in series.

The transfer gate 261 of the bit storage unit 242-$n$ includes two transistors 291 and 292, which are an NMOS transistor and a PMOS transistor, respectively.

The latch storage unit 262 of the bit storage unit 242-$n$ includes a static latch circuit including transistors 301 to 306. The transistors 301, 302, and 305 are PMOS transistors, while the transistors 303, 304, and 306 are NMOS transistors.

The output signal VCO, which is the output from the comparison circuit 51, is input to the inverter 281 and the NOR circuit 283, while the WORD signal is supplied to the other input of the NOR circuit 283. The output of the inverter 281 is supplied to the inverter 282 and the gate of the transistor 303 of the latch storage unit 262, while the output of the inverter 282 is supplied to the gate of the transistor 302 of the latch storage unit 262. In addition, the output of the NOR circuit 283 is supplied to the inverter 284 and the gate of the transistor 292 of the transfer gate 261, while the output of the inverter 284 is supplied to the gate of the transistor 291 of the transfer gate 261.

During the AD conversion period during which the sweep of the reference signal REF is performed, the N shift registers 341 of the time code transfer unit 23 transfer the time code supplied from the time code generation unit 26 by a shift clock having a unit time of the time code as a clock cycle.

During the time code write operation, the Hi write control signal WR and the Lo read control signal RD are supplied to the bidirectional buffer circuit 371. The bidirectional buffer circuit 371 supplies the time code supplied from a predetermined D-F/F 351 of the shift register 341 to the bit storage unit 242 via the transfer gate 261. The bit storage unit 242 stores the supplied time code.

In the subsequent time code read operation, the time code stored in the bit storage unit 242 is supplied to a predetermined D-F/F 351 of the shift register 341 of the time code transfer unit 23 via the bidirectional buffer circuit 371. The shift register 341 transfers the time data supplied to the D-F/F 351 of each stage forward to the output unit 28 and outputs the time data.

More specifically, each of the D-F/Fs 351 of the shift register 341 adopts a configuration in which the clock signal CLK supplied to the clock input can be brought into a high impedance state (hereinafter, referred to as a Hi-Z state) with one of Hi and Lo. For example, in a configuration of a D-F/F 351 described below with reference to FIG. 17, the D-F/F 351 becomes the Hi-Z state when the clock signal CLK is Lo.

During a period in which each of the D-F/Fs 351 of the shift register 341 is in the Hi-Z state, the Hi read control signal RD is supplied to the bidirectional buffer circuit 371. Together with this, the WORD signal becomes Hi, and the time code stored in the bit storage unit 242 is supplied to a predetermined D-F/F 351 of the shift register 341 of the time code transfer unit 23 via the bidirectional buffer circuit 371.

After the read control signal RD is returned to Lo, the shift clock is supplied to each of the D-F/Fs 351 of the shift register 341. The shift register 341 sequentially transfers the time data supplied to the D-F/F 351 of each stage to the output unit 28 and outputs the time data.

Figure 17:
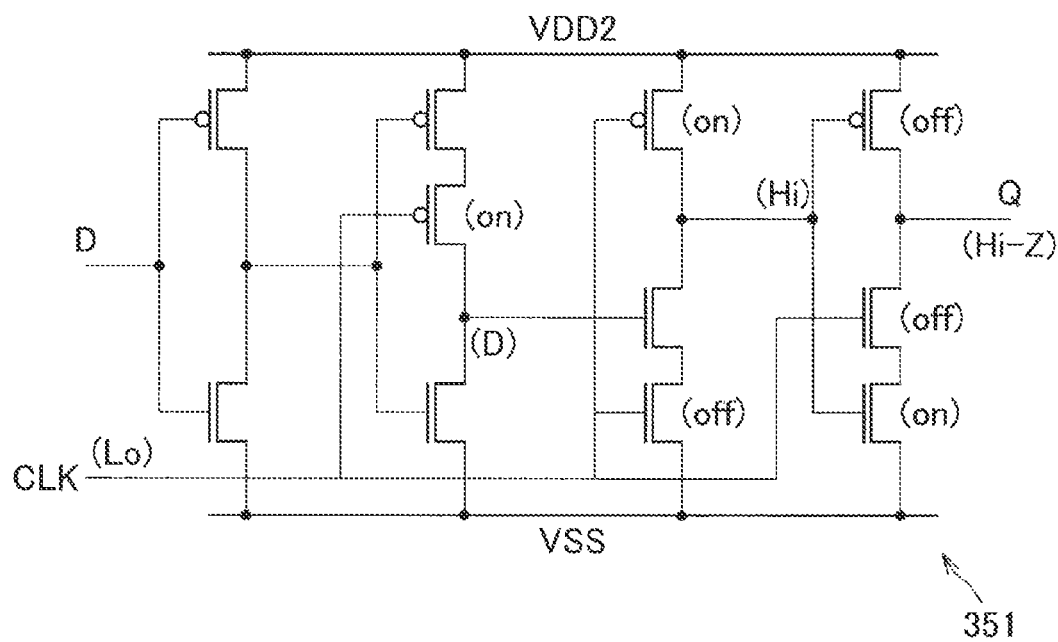
FIG. 17 is a diagram illustrating a circuit configuration of flip-flip of a shift register used in the time code transfer unit 23.

FIG. 17 is a diagram illustrating a circuit configuration of flip-flip of a shift register used in the time code transfer unit 23.

In FIG. 17, characters such as on and off written in parentheses ( ) in the vicinity of each of transistors and signal lines indicate the potential states of the individual transistors and signal lines when the Lo clock signal CLK is input to the clock input.

As illustrated in FIG. 17, when the Lo clock signal CLK is input to the D-F/F 351, the D-F/F 351 becomes the Hi-Z state.

Figure 18:
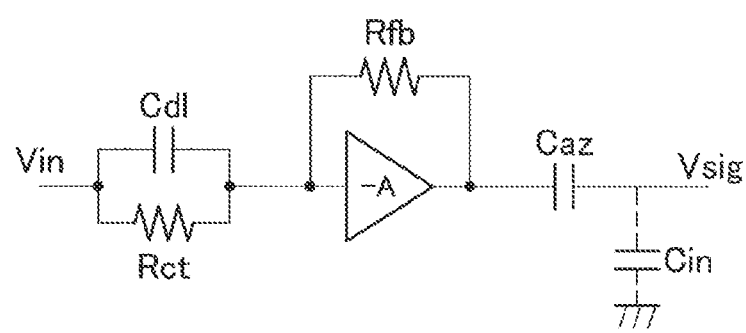
FIG. 18 is a diagram illustrating a circuit configuration of a preceding stage of the comparison circuit 51 at a first stage of the electrode 902, the amplifier circuit 901, and the AD conversion circuit 21.

Next, a transfer function for a path until a minute potential fluctuation Vin of the electrode 902 reaches an input node Vsig of the comparison circuit 51 at the first stage of the AD conversion circuit 21 will be examined. FIG. 18 is a diagram illustrating a circuit configuration of a preceding stage of the comparison circuit 51 at a first stage of the electrode 902, the amplifier circuit 901, and the AD conversion circuit 21. The relationship between Vin and Vsig is expressed as follows.

$$\frac{v_{sig}}{v_{in}} = -\frac{C_{az}}{C_{az} + C_{in}} \cdot \frac{R_{fb}A}{R_{fb} + R_{ct}(1+A)} \cdot \frac{1 + sR_{ct}C_{dl}}{1 + s\frac{R_{fb}R_{ct}C_{dl}}{R_{fb} + R_{ct}(1+A)}}$$

In the low frequency region where the signal frequency is extremely less than $1/2\pi R_{ct}C_{dl}$, the relationship is expressed as:

$$\frac{v_{sig}}{v_{in}} \approx -\frac{C_{az}}{C_{az} + C_{in}} \cdot \frac{R_{fb}A}{R_{fb} + R_{ct}(1+A)}$$

Furthermore, when $A \gg 1$ and $A \gg R_{fb}/R_{ct}$, the relationship is expressed as:

$$\frac{v_{sig}}{v_{in}} \approx -\frac{C_{az}}{C_{az} + C_{in}} \cdot \frac{R_{fb}}{R_{ct}}$$

In contrast, in a high frequency region where the signal frequency is extremely larger than $(R_{fb}+R_{ct}(1+A))/2\pi R_{fb}R_{ct}C_{dl}$, the relationship is expressed as:

$$\frac{v_{sig}}{v_{in}} \approx -\frac{C_{az}}{C_{az} + C_{in}}A$$

Figure 19:
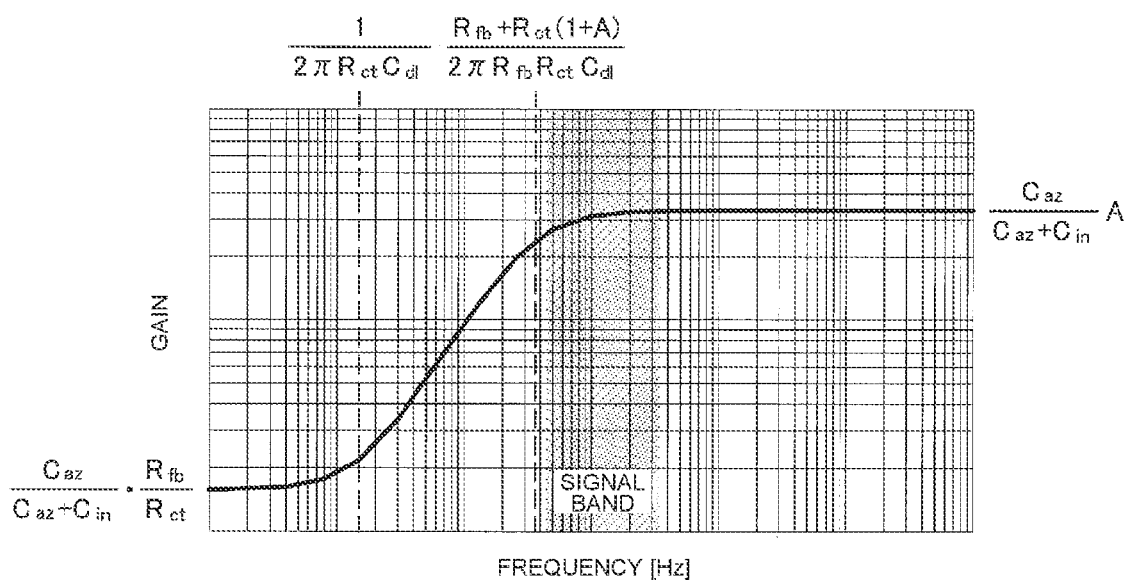
FIG. 19 is a diagram illustrating frequency characteristics of a gain.

From these, the frequency characteristic with respect to the gain indicates a high-pass filter (HPF) characteristic as illustrated in FIG. 19. When the action potential of the nerve cell is acquired, the signal band is considered to be in several hundred Hz to several kHz, and it is desirable that the gain outside the signal band drops from the viewpoint of noise characteristics. It is considered that the above-described HPF characteristics can suppress low frequency noise on the culture medium. Note that high frequency noise can be suppressed by a low-pass filter (LPF) characteristic of AD conversion.

In addition, the above formula indicates that the gain in the signal band takes a form of dividing an open-loop gain A of the amplifier circuit 901 by an inverse ratio of the DC cut capacitance Caz and the Vsig node parasitic capacitance Cin. In other words, the DC cut capacitance Caz can be reduced by increasing the open-loop gain A of the amplifier circuit 901 with respect to the gain desired to be finally obtained. Since the capacitance typically takes a large area, this will be a great advantage for the present embodiment having a need to mount the AD conversion circuit 21 within approximately 10 μm square size of the electrode 902.

2. Summary

As described above, according to the embodiment of the present disclosure, it is possible to provide the potential measurement device 1 that suppresses deterioration in noise and the sampling rate, and variation in offset. Specifically, the potential measurement device 1 according to the embodiment of the present disclosure has a structure including the first substrate 100 on which the electrode array is arranged and the second substrate 200 on which the AD conversion circuit array is arranged and which is stacked with respect to the first substrate 100.

With such a configuration, the potential measurement device 1 according to the embodiment of the present disclosure can minimize the wiring length from the output of the amplifier circuit to the AD conversion circuit, and can substantially equalize the length of each of wiring lines. Accordingly, the potential measurement device 1 according to the embodiment of the present disclosure can improve the sampling rate by reducing the wiring capacitance, and can also improve the sampling rate by reducing the offset variation of the amplifier output, which can be achieved by substantially equalizing the wiring length that has been different for each of cells.

The preferred embodiments of the present disclosure have been described in detail above with reference to the accompanying drawings. However, the technical scope of the present disclosure is not limited to such examples. It will be apparent to those skilled in the art of the present disclosure that various modifications and alterations can be conceived within the scope of the technical idea described in the claims and naturally fall within the technical scope of the present disclosure.

Furthermore, the effects described in the present specification are merely illustrative or exemplary and are not limited. That is, the technique according to the present disclosure can exhibit other effects that are apparent to those skilled in the art from the description of the present specification in addition to or instead of the above effects.

Note that the following configurations also belong to the technical scope of the present disclosure.

(1)

A potential measurement device comprising:

a first substrate having read electrodes arranged in a two-dimensional array; and a second substrate on which the first substrate is stacked, wherein each of the read electrodes includes at least one or more AD conversion circuits each having independent correspondence to the read electrode, and at least a part of the AD conversion circuits is arranged in a two-dimensional array on the second substrate.

(2)

The potential measurement device according to (1), wherein wiring is performed such that wiring lengths of signal paths from the read electrode to the AD conversion circuit are substantially equal.

(3)

The potential measurement device according to (2), further comprising an amplifier circuit in the signal path from the read electrode to the AD conversion circuit.

(4)

The potential measurement device according to (3), wherein the amplifier circuit is a source follower circuit including: an amplifier transistor whose drain terminal is grounded AC-wise; and a load.

(5)

The potential measurement device according to (3), wherein the amplifier circuit is a common-source amplifier circuit including: an amplifier transistor whose source terminal is grounded AC-wise; and a load.

(6)
The potential measurement device according to (4) or (5), wherein input/output connection of the amplifier circuit is made by a feedback resistor.
(7)
The potential measurement device according to (6), wherein the feedback resistor has a variable resistance value.
(8)
The potential measurement device according to (4) or (5), wherein a bias voltage is applied to the input of the amplifier circuit via a resistor.
(9)
The potential measurement device according to any one of (1) to (8),
wherein the AD conversion circuit includes a comparison circuit, and
the comparison circuit receives, at one input, application of an input signal via a DC cut capacitance, and receives, at the other input, application of a reference signal that changes with time.
(10)
The potential measurement device according to (9), further comprising:
a data storage unit that stores data corresponding to an output of the comparison circuit; and
a data transfer circuit that performs writing of data to the data storage unit and reading of data from the data storage unit by an identical circuit.
(11)
The potential measurement device according to any one of (1) to (10), wherein the AD conversion circuit corresponds to a plurality of the read electrodes.

REFERENCE SIGNS LIST

1 POTENTIAL MEASUREMENT DEVICE
21 AD CONVERSION CIRCUIT
22 AD CONVERSION CIRCUIT ARRAY
23 TIME CODE TRANSFER UNIT
24 PIXEL DRIVE CIRCUIT
26 TIME CODE GENERATION UNIT
27 VERTICAL DRIVE CIRCUIT
28 OUTPUT UNIT
29 TIMING GENERATION CIRCUIT
37 BIDIRECTIONAL BUFFER CIRCUIT
51 COMPARISON CIRCUIT
52 DATA STORAGE UNIT
61 DIFFERENTIAL INPUT CIRCUIT
62 VOLTAGE CONVERSION CIRCUIT
63 POSITIVE FEEDBACK CIRCUIT
900 READ ELECTRODE ARRAY
901 AMPLIFIER CIRCUIT
902 ELECTRODE
910 REFERENCE ELECTRODE

The invention claimed is:

1. A potential measurement device, comprising:
a first substrate having a plurality of read electrodes arranged in a two-dimensional array;
a second substrate on which the first substrate is stacked, wherein
each read electrode of the plurality of read electrodes is associated with one or more AD conversion circuits,
each AD conversion circuit of the one or more AD conversion circuits has independent correspondence to a read electrode of the plurality of read electrodes, and
at least a part of the one or more AD conversion circuits is arranged in a two-dimensional array on the second substrate; and
an amplifier circuit in a signal path from each read electrode of the plurality of read electrodes to each AD conversion circuit of the one or more AD conversion circuits.

2. The potential measurement device according to claim 1, wherein
wiring is such that wiring lengths of signal paths from each read electrode of the plurality of read electrodes to each AD conversion circuit of the one or more AD conversion circuits are substantially equal.

3. The potential measurement device according to claim 1, wherein the first substrate further includes the amplifier circuit.

4. The potential measurement device according to claim 1, wherein
the amplifier circuit is a source follower circuit including:
an amplifier transistor whose drain terminal is grounded AC-wise; and
a load.

5. The potential measurement device according to claim 1, wherein
the amplifier circuit is a common-source amplifier circuit including:
an amplifier transistor whose source terminal is grounded AC-wise; and
a load.

6. The potential measurement device according to claim 4, wherein input/output connection of the amplifier circuit is by a feedback resistor.

7. The potential measurement device according to claim 6, wherein the feedback resistor has a variable resistance value.

8. The potential measurement device according to claim 4, wherein a bias voltage is applied to an input of the amplifier circuit via a resistor.

9. The potential measurement device according to claim 1, wherein
each AD conversion circuit of the one or more AD conversion circuits includes a comparison circuit, and
the comparison circuit is configured to:
receive, at a first input, application of an input signal via a DC cut capacitances; and
receive, at a second input, application of a reference signal that changes with time.

10. The potential measurement device according to claim 9, further comprising:
a data storage unit configured to store data corresponding to an output of the comparison circuit; and
a data transfer circuit configured to:
write data to the data storage unit; and
read data from the data storage unit based on an identical circuit.

11. The potential measurement device according to claim 1, wherein an AD conversion circuit of the one or more AD conversion circuits corresponds to the plurality of the read electrodes.

* * * * *